United States Patent [19]

Sakoda et al.

[11] Patent Number: 5,051,337

[45] Date of Patent: Sep. 24, 1991

[54] OPTICAL RECORDING MATERIAL

[75] Inventors: Kazuaki Sakoda; Kazuhiko Kominami; Masao Iwamoto, all of Otsu, Japan

[73] Assignee: Director-General of Agency of Industrial Science and Technology, Japan

[21] Appl. No.: 517,537

[22] Filed: Apr. 24, 1990

Related U.S. Application Data

[63] Continuation of Ser. No. 202,119, Jun. 2, 1988, abandoned.

[30] Foreign Application Priority Data

| Jun. 10, 1987 | [JP] | Japan | 62-143291 |
| Dec. 9, 1987 | [JP] | Japan | 62-309448 |
| Dec. 9, 1987 | [JP] | Japan | 62-309449 |

[51] Int. Cl.$^5$ .................. G11C 13/04; G03C 1/73
[52] U.S. Cl. ..................... 430/270; 430/495; 430/945; 346/135.1; 365/119
[58] Field of Search ........... 430/495, 945, 270; 346/135.1; 540/145; 365/119

[56] References Cited

U.S. PATENT DOCUMENTS

| 4,101,976 | 7/1978 | Castro et al. | 365/119 |
| 4,614,723 | 9/1986 | Schmidt et al. | 540/145 |

FOREIGN PATENT DOCUMENTS 1260377 9/1986 U.S.S.R.

OTHER PUBLICATIONS

S. Volker et al.: IBM J. Res Development, vol. 23, No. 5, Sep. 1979, pp. 547-555.

S. Volker et al.: The Journal of Chemical Physics, vol. 67, No. 4 (Aug. 15, 1977) pp. 1759-1765.
A. R. Gutierrez et al.: IBM J.Res Develop., vol. 26, No. 2, Mar. 1982, pp. 198-208.

*Primary Examiner*—Charles L. Bowers, Jr.
*Assistant Examiner*—Mark R. Buscher
*Attorney, Agent, or Firm*—Austin R. Miller

[57] ABSTRACT

Disclosed is an optical recording material comprising a porphine derivative having at least an ionic group and a polymer compatible with this porphine derivative. As the porphine derivative, there are used a porphine derivative having an N-alkylpyridinium group, such as 5,10,5,20-tetra(4-N-methylpyridinium) porphine, a porphine derivative having a quaternary amino group, such as 5,10,15,20-tetra(4-N,N,N-trimethylaminophenyl) porphine, a porphine derivative having a sulfonatophenyl group, such as 5,10,15,20-tetra (4-sulfonatophenyl) porphine, and a porphine derivative having a carbonatophenyl group, such as 5,10,15,20-tetra-(4-carbonatophenyl) porphine. Either an organic polymer or an inorganic polymer is used as the polymer. From the viewpoint of the recording stability, a water-soluble polymer such as polyvinyl alcohol or sodium polystyrene sulfonate is preferred as the organic polymer. Silica glass synthesized by using tetramethoxysilane or tetraethoxysilane as the starting material is used as the inorganic polymer.

In the optical recording material, a thermally stable hole can be formed at a temperature higher than the liquid helium temperature, and therefore, attenuation of the formed holes after elevation of the temperature is small and the recording stability is high. Moreover, a formation of hole at the liquid nitrogen temperature can be carried out.

20 Claims, 9 Drawing Sheets

OPTICAL RECORDING MATERIAL this application is a continuation of application Ser. No. 202,119, filed June 2, 1988, now abandoned.

BACKGROUND OF THE INVENTION (1.) Field of the Invention

The present invention relates to an optical recording material for use in a frequency selective optical data recording and storage system in which multiplex recording on the same site of one material can be performed with lights differing in wavelength by utilizing the technique of photochemical hole burning.

(2.) Description of the Related Art

The photochemical hole burning (hereinafter referred to as "PHB") is a phenomenon in which, when a material causing a photochemical reaction at an ultralow temperature such as the temperature of liquid helium is irradiated with a light having good monochromaticity, only the molecule absorbing this light is selectively excited to cause a photochemical change. Since sharp holes (dents) are formed in the light absorption spectrum of the material by this photochemical change, the formation of an optical memory becomes possible according to the presence or absence of the holes. Moreover, if recording is carried out in succession by using irradiation lights differing in wavelength, wavelength-multiplexed recording can be performed on the same site of one material. If this wavelength-multiplexed recording method is adopted, a possibility exists that the recording density will be improved to a level of about 1,000 times higher than the recording density attainable in a conventional optical digital recording medium such as a compact disk or a laser disk.

An optical recording material utilizing this PHB phenomenon comprises guest molecules, which are photoreactive compounds, and a host for dispersing these guest molecules. To increase the wavelength multiplicity in an optical recording, it is sufficient if the dispersion state of the guest is varied, and the use of an amorphous substance as the host is preferred for this purpose. Therefore, a polymer or silica glass has been used as the host.

As typical instances of the conventional PHB material, there are known a material comprising free-base porphine represented by the formula shown in FIG. 1 as the guest and an aliphatic hydrocarbon as the host; a material comprising tetraphenylporphine represented by the formula shown in FIG. 2 as the guest and a polymer such as polymethyl methacrylate as the host [Japanese Journal of Optics, 14, (4), 263–269]; a material comprising Cresyl Violet represented by the formula shown in FIG. 3 as the guest and polyvinyl alcohol as the host; a material comprising quinizarin represented by the formula shown in FIG. 4 as the guest and silica glass as the host [J. Appl. Phys., 58, (9), 3559–3565]; and a material comprising phthalocyanine represented by the formula shown in FIG. 5 as the guest and an aliphatic hydrocarbon as the host.

With respect to the temperature characteristics of PHB materials, Thijssen et al reported a formation of holes at temperatures lower than 30K [Chem. Phys. Lett., 92, (2), 7–12], and Tani et al reported a reservation of holes at temperatures lower than 60K [J. Appl. Phys., 58, (9), 3559–3565].

In the conventional PHB materials, the half width of the formed holes increases as the temperature rises and the wavelength multiplicity of a recording is drastically decreased. To put wavelength-multiplexed recording to practical use, for the reasons set forth below, it is necessary to develop a PHB material in which this defect is alleviated as much as possible.

In the first place, recording is made in the PHB material and is then read out, and the temperature of the material must be maintained at a low level during this period by using a coolant such as liquid helium. But, a temperature deviation inevitably occurs in the cooling apparatus, and the PHB material to be used must stably retain the recording state even if the material undergoes this temperature deviation. In the second place, the PHB material is irradiated with light for writing information, and at the time of irradiation, the temperature of the material is elevated by the absorption of light. This elevation of the temperature is conspicuous when the writing of information is carried out at a high speed by increasing the irradiation intensity. Therefore, the PHB material to be used must have properties such that recording can be stably performed even if the material is exposed to this elevated temperature.

Moreover, in the case of the conventional PHB materials, it is impossible to form holes at the temperature of liquid nitrogen. But, there is a demand for developing a PHB material in which holes can be formed at the liquid nitrogen temperature, since this is practically advantageous because the cooling cost is drastically reduced.

SUMMARY OF THE INVENTION

It is an object of the present invention to provide an optical recording material comprising a porphine derivative having an ionic group as the photoreactive guest compound and a polymer compatible with the guest compound as the host component, which are characterized in that thermal irreversible changes are controlled, an attenuation of formed holes after elevation of the temperature is reduced and the recording stability is high.

Another object of the present invention is to provide an optical recording material in which a formation of holes can be expected even at the liquid nitrogen temperature.

The optical recording material is comprised of a composition comprising a guest component and a host component as main components, wherein the guest component is a porphine derivative having at least one ionic group and the host component is a polymer having compatibility with the guest component. The ionic group-containing porphine derivative is represented by the following general formula (I):

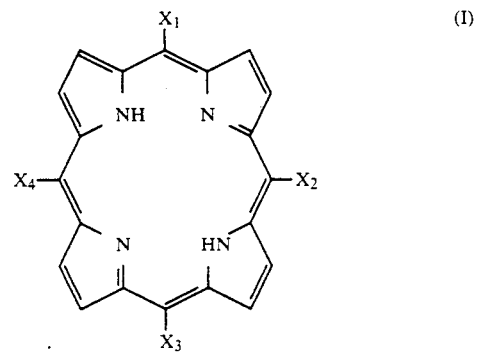

wherein at least one of $X_1$, $X_2$, $X_3$ and $X_4$ is an aryl group having an ionic group or an ionic heterocyclic group having an alkyl group of 1 to 6 carbon atoms, and the other thereof is a hydrogen atom or a non-ionic organic group.

DESCRIPTION OF THE PREFERRED EMBODIMENTS

The ionic group in the porphine derivative of the formula (I) of this invention may be any of a cationic group, an anionic group and an amphoteric group.

Figure 1:
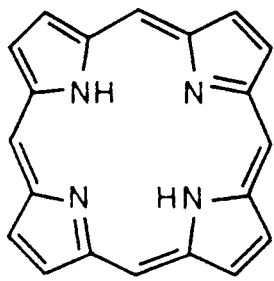
FIG. 1 shows the chemical formula of free base porphine used as the guest in a conventional PHB material.
Figure 2:
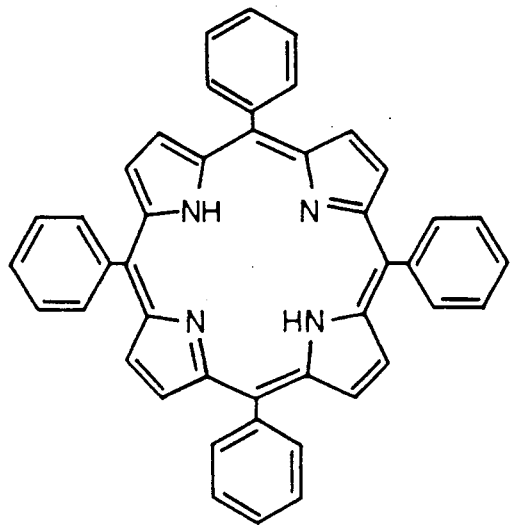
FIG. 2 shows the chemical formula of tetraphenylporphine used as the guest in a conventional PHB material.
Figure 3:
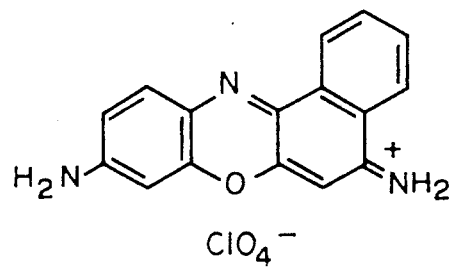
FIG. 3 shows the chemical formula of Cresyl Violet used as the guest in a conventional PHB material.
Figure 4:
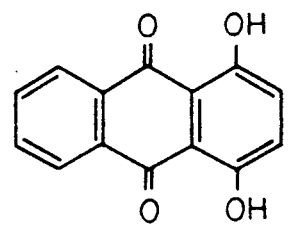
FIG. 4 shows the chemical formula of quinizarin used as the guest in a conventional PHB material.
Figure 5:
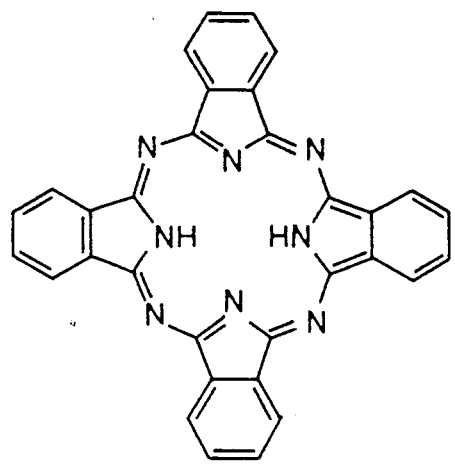
FIG. 5 shows the chemical formula of phthalocyanine used as the guest in a conventional PHB material.
Figure 6:
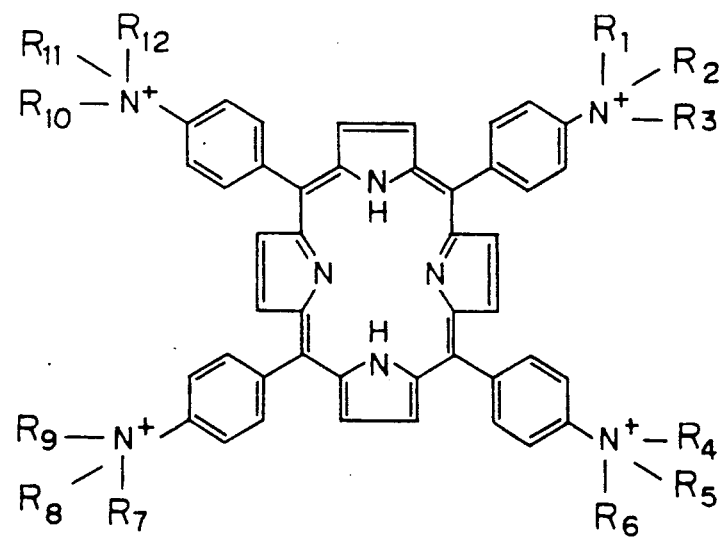
FIG. 6 shows the chemical formula of 5,10,15,20-tetra(4-N,N,N-trialkylaminophenyl)porphine used as a guest in the PHB material of the present invention.
Figure 7:
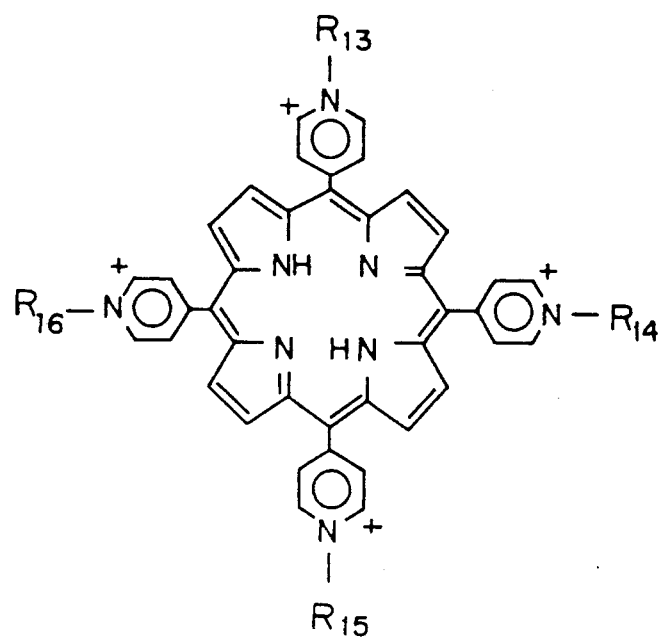
FIG. 7 shows the chemical formula of 5,10,15,20-tetra(4-N-alkylpyridinium)porphine used as another guest in the PHB material of the present invention.
Figure 8:
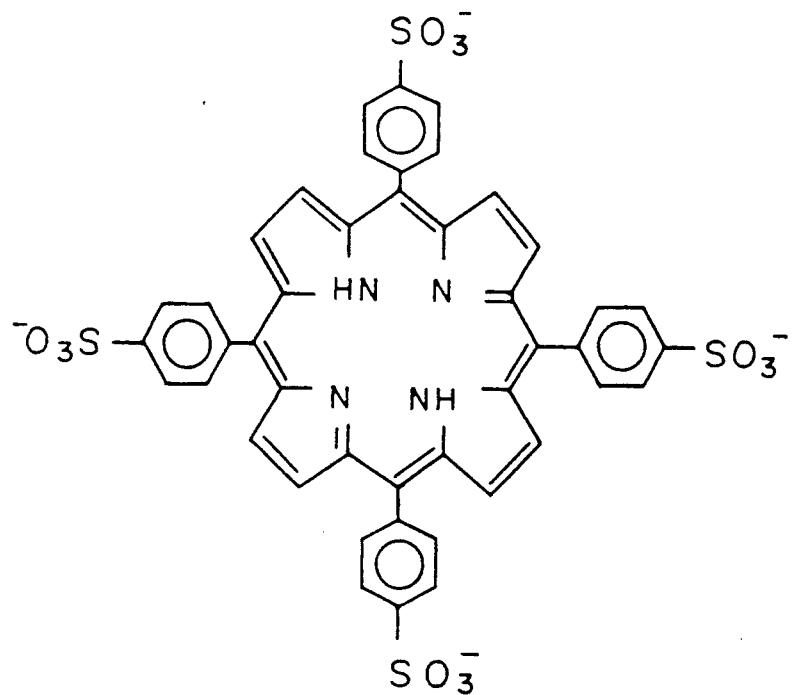
FIG. 8 shows the chemical formula of 5,10,15,20-tetra(4-sulfonatophenyl)porphine used as yet another guest in the PHB material of the present invention.
Figure 9:
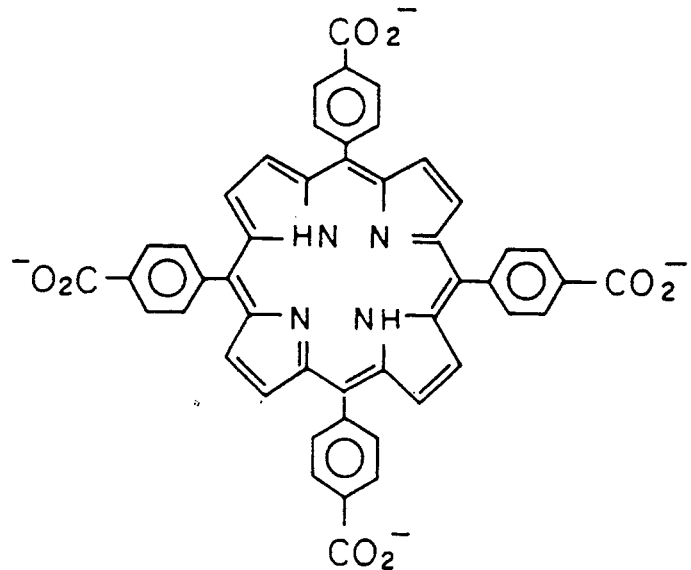
FIG. 9 shows the chemical formula of 5,10,15,20-tetra(4-carbonatophenyl)porphine used as still another guest in the PHB material of the present invention.

As the cationic group, a quaternary ammonium group is preferred; especially a 5,10,15,20-tetra(4-N,N,N-trialkylaminophenyl)porphine represented by the chemical formula shown in FIG. 6 is preferred. As the ionic heterocyclic group having an alkyl group, an N-alkylpyridinium group is preferred; especially a 5,10,15,20-tetra(4-N-alkylpyridinium)porphine represented by the chemical formula shown in FIG. 7 is preferred. $R_1$ through $R_{12}$ in the formula of FIG. 6 and $R_{13}$ through $R_{16}$ in the formula of FIG. 7 stand for an alkyl group having 1 to 6 carbon atoms.

The reasons why these compounds are preferably used are that in the porphine derivative of the formula shown in FIG. 6, the porphine ring is spaced from the quaternary ammonium group through the phenyl group and in the porphine derivative of the formula shown in FIG. 7, the charge of the pyridinium group is dispersed in the conjugate system, and thus, the cationic group has little influence on the photochemical reactivity of the porphine ring. An alkyl group having a small carbon number is preferred for $R_1$ through $R_{12}$ in the formula of FIG. 6 and $R_{13}$ through $R_{16}$ in the formula of FIG. 7, and a methyl group is most preferred. It is presumed that this is because, if the carbon number of the alkyl group is small and the structure is compact, the freedom of movement is small when the compound is dispersed in the host, and thus, an irreversible structural change rarely occurs at low temperatures. This porphine derivative having a cationic group is present together with an appropriate anion in the material. The anion is selected in view of compatibility with the host component, and a p-toluenesulfonate ion, $I^-$, $Br^-$, $Cl^-$, $ClO_4^-$, $CH_3CO_2^-$ and $BF_4^-$ are preferably used.

Figure 10:
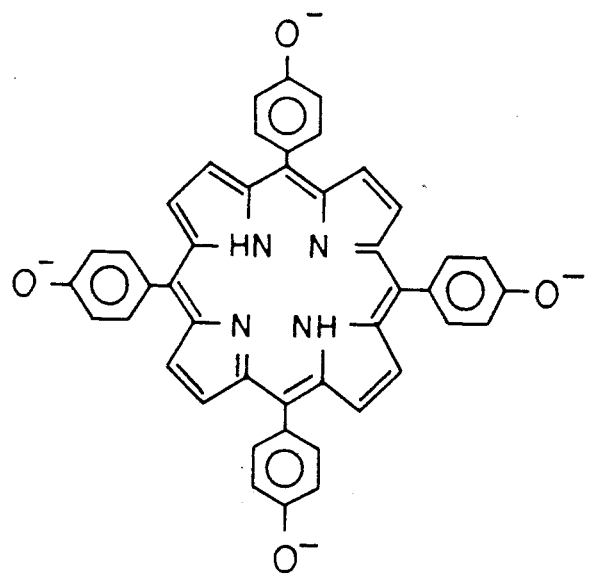
FIG. 10 shows the chemical formula of 5,10,15,20-tetra(4-phenoxido)porphine used as still another guest in the PHB material of the present invention.

An $SO_3^-$ group, a $CO_2^-$ group and an $O^-$ group are preferably used as the anionic group, because these groups stably keep an ionospheric state in the host. Among these porphine derivatives having an anionic group, 5,10,15,20-tetra(4-sulfonatophenyl)porphine represented by the chemical formula shown in FIG. 8, 5,10,15,20-tetra(4-carbonatophenyl)porphine represented by the chemical formula shown in FIG. 9, and 5,10,15,20-tetra(4-phenoxido)porphine represented by the chemical formula in FIG. 10 are especially preferable. This is because in these anionic porphine derivatives, the porphine ring is spaced from the anionic group through the phenyl group and hence, the ionic group has little influence on the photochemical reactivity of the porphine ring. Such a porphine derivative having an anionic group is present together with an appropriate cation in the material. The cation is selected in view of the compatibility with the host component, and an alkali metal ion, a hydrogen ion, an alkaline earth metal ion and an ammonium ion are preferred as the cation.

As the porphine derivative having an amphoteric group, there are preferably used tetra [3-(N-sulfonatoalkyl-N-alkylamino)phenyl] porphines, tetra[3-(N-carbonatoalkyl-N-alkylamino)phenyl] porphines, tetra[4-(N-sulfonatoalkyl)pridinium] porphines and tetra [4-(N-carbonatoalkyl)pyridinium] porphines. Each of the alkyl groups in these porphine derivatives has 1 to 6 carbon atoms.

In the porphine derivatives represented by the formula (I), part of $X_1$, $X_2$, $X_3$ and $X_4$ may be a hydrogen atom or a non-ionic organic group such as, for example, phenyl group, methoxyphenyl group, nitrophenyl group, naphthyl group or methoxynaphthyl group.

The 5,10,15,20-tetra(4-N,N,N-trialkylaminophenyl)-porphine represented by the formula shown in FIG. 6 is obtained by hydrolyzing 5,10,15,20-tetra(4-acetaminophenyl)phosphine, synthesized from acetaminobenzaldehyde and pyrrole, with an acid and reacting the hydrolysis product with a quaternizing agent such as an alkyl iodide. The 5,10,15,20-tetra(4-N-alkylpyridinium)- porphine represented by the formula shown in FIG. 7 is obtained by quaternizing 5,10,15,20-tetra(4-pyridyl)porphine with a quaternizing agent such as an alkyl iodide. Furthermore, the porphine derivatives having an anionic group, which are represented by the formulae shown in FIGS. 9, 10 and 11, can be obtained by reacting 5,10,15,20-tetraphenylporphine with a polybasic acid or from a precursor synthesized from a benzaldehyde derivative having a group that can be converted to an anionic group and pyrrole.

A polymer compatible with the guest component is used as the host in the present invention, and either an organic polymer or an inorganic polymer can be used.

As the organic polymer, there are preferably used water-soluble polymers such as polyethylene oxide, polyvinyl pyridine, polyvinyl pyrrolidone, polymethacrylic acid, polyacrylic acid, polymethacrylamide, polyacrylamide, cellulose acetate, sodium polyvinyl sulfonate, sodium polystyrene sulfonate and polyvinyl alcohol; especially preferred are polyvinyl alcohol and sodium polystyrene sulfonate. Since the porphine derivative having an ionic group, which is used as the guest component, is soluble in a polar solvent, the porphine derivative is compatible with these water-soluble polymers and can be easily dispersed. It is presumed that little thermal structural change occurs at low temperatures in polyvinyl alcohol, because polyvinyl alcohol has a strong hydrogen-bonding property, and since sodium polystyrene sulfonate has a benzene ring in the side chain, sodium polystyrene sulfonate has a high affinity with the guest component. Therefore, polyvinyl alcohol and sodium polystyrene sulfonate are especially preferred.

Silica glass is preferably used as the inorganic polymer. It is sufficient if silica glass is compatible with the guest, but, silica glass synthesized from tetramethoxysilane or tetraethoxysilane is preferred because the guest compound can be dispersed in the monomer solution for silica glass and this dispersion state is not destroyed by a polymerization reaction using a weak acid or weak base.

If the concentration of the guest component in the optical recording material of the present invention is too high, the hole-forming characteristics are degraded by the transfer of energy among molecules of the guest, and if the concentration of the guest component is too low, the S/N ratio is reduced at the recording and reading steps. Accordingly, the concentration of the guest is preferably $10^{-1}$ to $10^{-5}$M, especially $10^{-2}$ to $10^{-4}$M, based on the volume of the polymer as the host.

In the optical recording material of the present invention, the affinity between the guest and host is enhanced by an interaction based on the charge possessed by the ionic porphine, and therefore, it is presumed that the amount of irreversible structural change at an elevated temperature is reduced. Consequently, increase of the half width of holes in the absorption spectrum of the material is controlled, and the heat stability of the recording is improved. In addition, formation of holes at the liquid nitrogen temperature, which is impossible according to the conventional technique, can be carried out.

The present invention will now be described in detail with reference to the following examples that by no means limit the scope of the invention.

EXAMPLE 1

In 100 ml of distilled water was dissolved 10 g of polyvinyl alcohol having a polymerization degree of 2,000 and a saponification degree of 100%, and 0.13 g of 5,10,15,20-tetra(4-N,N,N-trimethylaminophenyl)porphine tetra(p-toluene-sulfonate) (supplied by Dojindo Laboratories) was added to the solution. The solution was dried in a Petri dish to obtain a film having a guest concentration of $10^{-2}$M and a thickness of 0.5 mm. The film was cooled to the liquid helium temperature and the film was irradiated with a laser beam having a wavelength of 646 nm and an intensity of 1 mW/cm$^2$ for 1 minute to form a PHB hole. Then, the temperature of the film was elevated to a predetermined level, the film was again cooled to the liquid helium temperature, and the half width of the PHB hole was measured.

Figure 11:
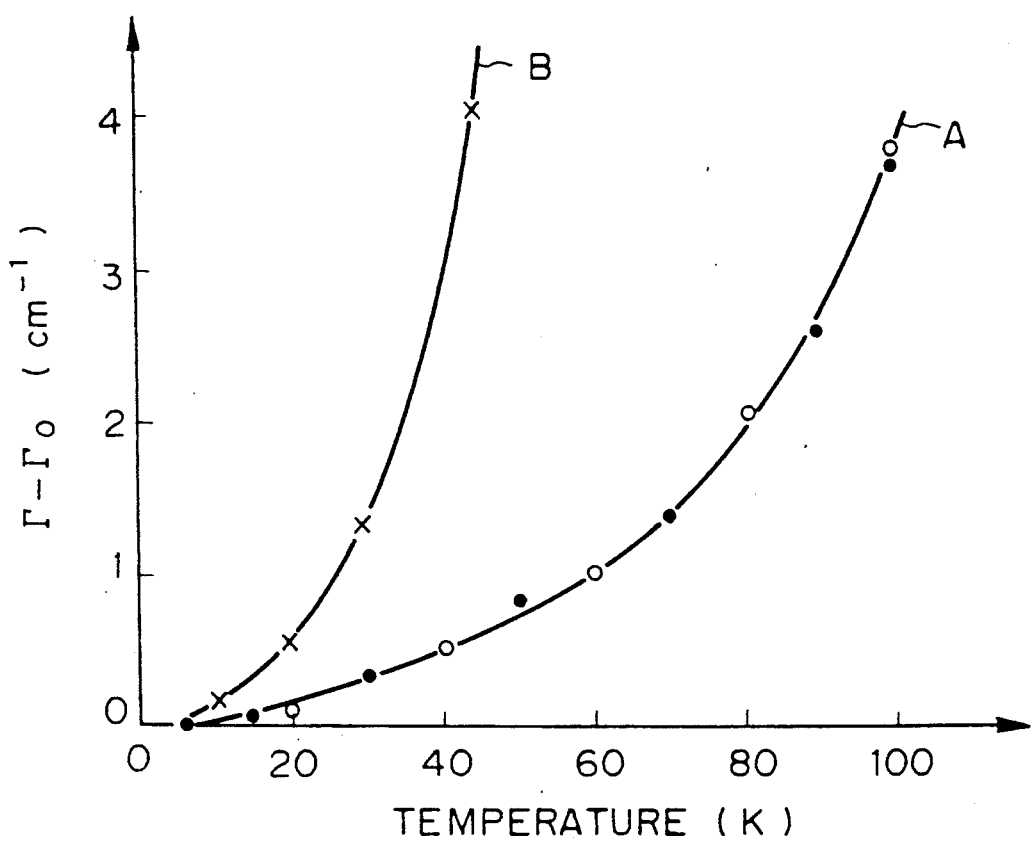
FIG. 11 is a diagram comparing performance of PHB holes formed in Examples 1 and 2 (curve A) with PHB holes formed in Comparative Example 1 (curve B) with respect to the increase of the half width after elevation of the temperature and re-cooling.

FIG. 11 illustrates the difference between the half width ($\Gamma_0$) of the PHB hole just after irradiation with a laser beam and the half width ($\Gamma$) after elevation of the temperature and recooling relatively to the elevated temperature. The curve A formed by connecting points "." shows the results obtained with respect to the sample obtained in Example 1. The curve B shows the results obtained in Comparative Example 1, mentioned below.

EXAMPLE 2

In 100 ml of distilled water was dissolved 10 g of polyvinyl alcohol having a polymerization degree of 2,000 and a saponification degree of 100%, and 0.1 g of 5,10,15,20-tetra(4-N-methylpyridinium)porphine tetraiodide (supplied by Wako Pure Chemical Industries) was added to the solution. The solution was dried in a Petri dish to obtain a film having a guest concentration of $10^{-2}$M and a thickness of 0.5 mm. A PHB hole was formed in this film in the same manner as described in Example 1. The temperature of the film was elevated to a predetermined level, the film was again cooled to the liquid helium temperature, and then the half width of the PHB hole was measured.

In FIG. 11, the results are shown by the curve formed by connecting points "o".

COMPARATIVE EXAMPLE 1

In 120 ml of toluene was dissolved 10 g of isotactic polymethyl methacrylate having a polymerization degree of 4,000, and 0.05 g of tetraphenylporphine was added to the solution. The solution was dried in a Petri dish to obtain a film having a guest concentration of $10^{-2}$M and a thickness of 0.5 mm as a comparative sample. In the same manner as described in Example 1, a PHB hole was formed on the film. The temperature of the film was elevated to a predetermined level and the film was cooled to the liquid helium temperature again, and the half width of the PHB hole was measured.

In FIG. 11, the curve B shows the obtained results.

It is seen that the samples obtained in Examples 1 and 2 (curve A) have a smaller increase of the half width of the PHB hole after elevation of the temperature and re-cooling and have an excellent heat stability.

EXAMPLE 3

In 100 ml of distilled water was dissolved 10 g of polyvinyl alcohol having a polymerization degree of 2,000 and a saponification degree of 100%, and 0.1 g of tetrasodium 5,10,15,20-tetra(4-sulfonatophenyl)porphine dodecahydrate (supplied by Wako Pure Chemical Industries) was added to the solution. The solution was dried in a Petri dish to obtain a film having a guest concentration of $10^{-2}$M and a thickness of 0.5 mm. A PHB hole was formed in the film in the same manner as described in Example 1. Then, the temperature of the film was elevated to a predetermined level, the film was again cooled to the liquid helium temperature, and the half width of the PHB hole was measured.

Figure 12:
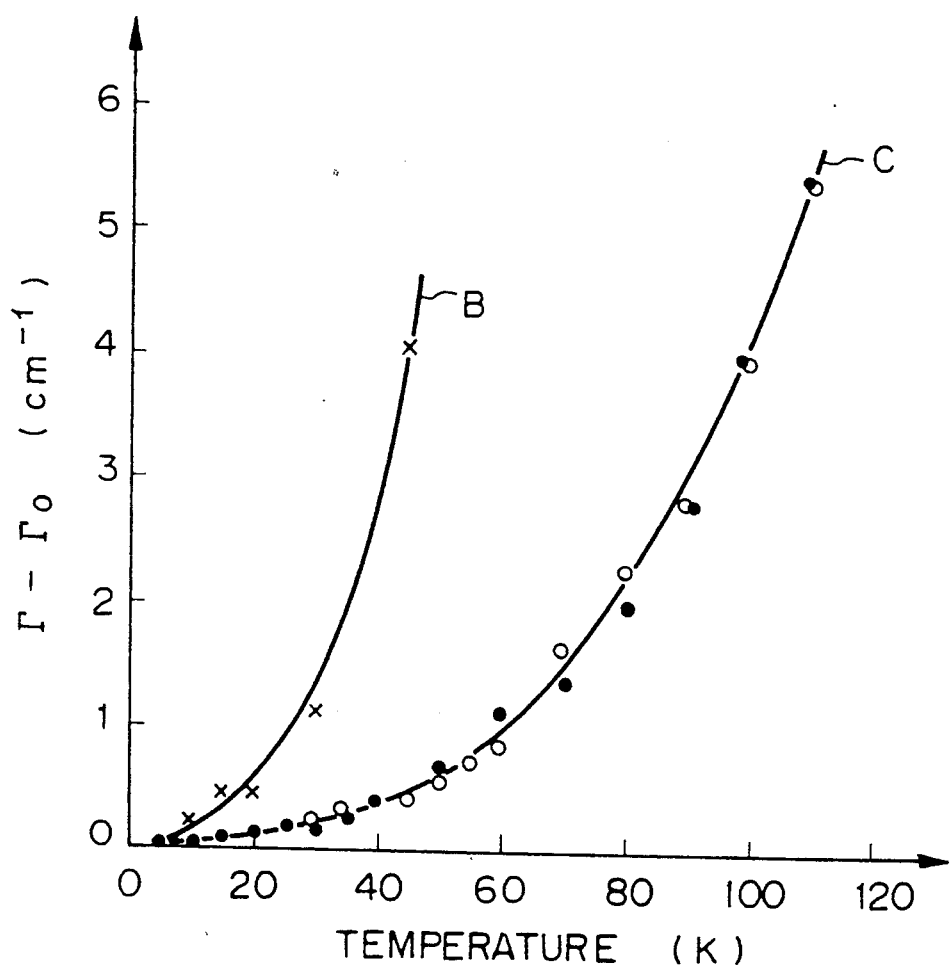
FIG. 12 is a diagram comparing performance of PHB holes formed in Examples 3 and 4 (curve C) with PHB holes formed in Comparative Example 1 (curve B) with respect to the increase of the half width after elevation of the temperature and re-cooling.

As in FIG. 11, the difference between ($\Gamma_0$) and ($\Gamma$) is shown in FIG. 12 relatively to the elevated temperature. The curve C obtained by connecting points "." shows the results obtained with respect to the sample of Example 3.

EXAMPLE 4

In refluxed propionic acid, 30 g of 4-carboxybenzaldehyde was reacted with 13.4 g of pyrrole to obtain 6.9 g of 5,10,15,20-tetra(4-carboxyphenyl)porphine. This porphine derivative was reacted with an aqueous solution containing four equivalents of sodium hydroxide to obtain tetrasodium 5,10,15,20-tetra(4-carbonatophenyl)porphine.

In 100 ml of distilled water was dissolved 10 g of polyvinyl alcohol having a polymerization degree of 2,000 and a saponification degree of 100%, and 0.07 g of tetrasodium 5,10,15,20-tetra(4-carbonatophenyl)porphine was added to the solution. The solution was dried in a Petri dish to obtain a film having a thickness of 0.5 mm. A PHB hole was formed in the film in the same manner as described in Example 1. Then, the temperature of the film was elevated to a predetermined level and the film was again cooled to the liquid helium temperature, and the half width of the PHB holes was measured.

The results are shown by the curve C obtained by connecting points "○" in FIG. 12.

In FIG. 12, the results obtained in Comparative Example 1 are shown by the curve B. When the results of Comparative Example 1 are compared with the results obtained in Examples 3 and 4, it is seen that the samples of Examples 3 and 4 have a smaller increase of the half width of the PHB hole after elevation of the temperature and re-cooling and have an excellent heat stability.

Formation of 5,10,15,20-tetra(4-carboxyphenyl)porphine was confirmed by the facts that a carbonyl stretching vibration was observed at 1,690 cm$^{-1}$ in the infrared absorption spectrum of the product, absorption bands attributed to the porphine ring were observed at 426, 510, 545, 586 and 642 nm in the visible-ultraviolet absorption spectrum of a methanol solution and only one spot was observed in the thin layer chromatography.

The formation of tetrasodium 5,10,15,20-tetra(4-carbonatophenyl)porphine was confirmed by a disappearance of the absorption at 1,690 cm$^{-1}$.

EXAMPLE 5

The same sample as obtained in Example 3 was irradiated with a laser beam at various sample temperatures to form PHB holes, and the half width of the holes was measured.

Figure 13:
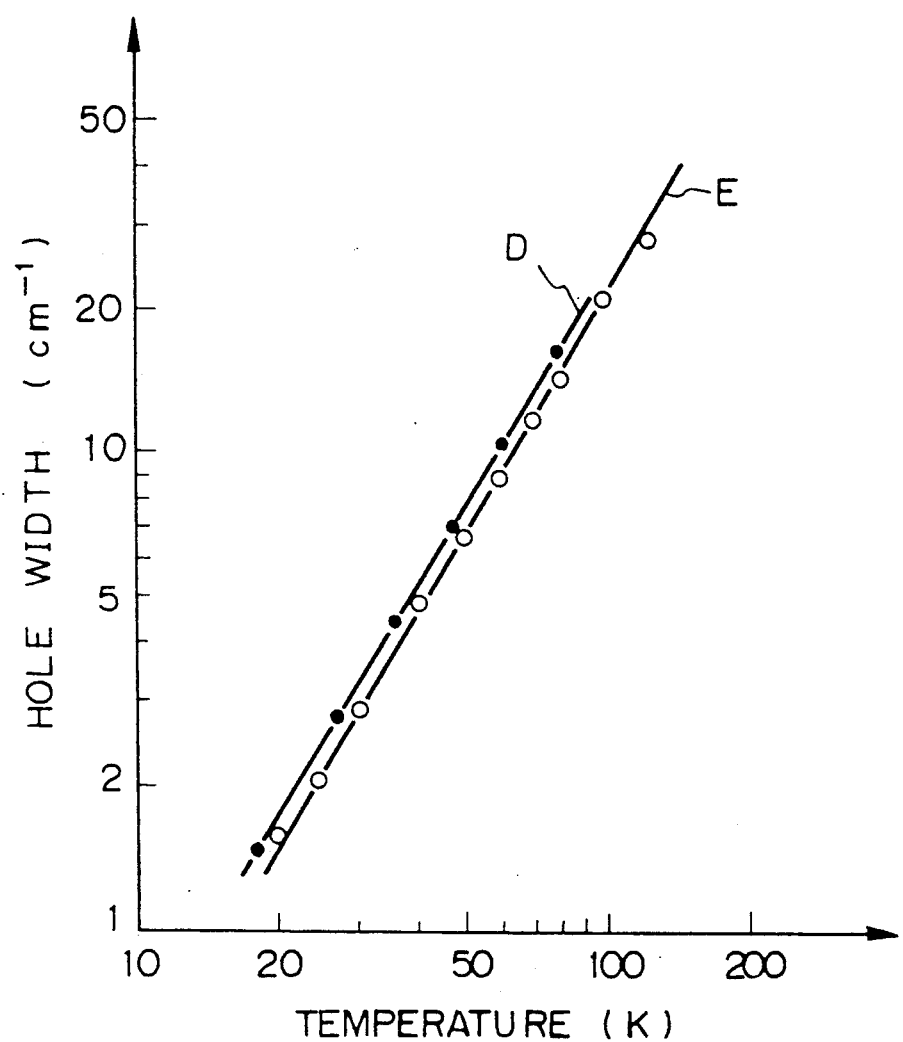
FIG. 13 is a diagram illustrating half widths of PHB holes formed at various temperatures on samples of Examples 5 (curve D) and 6 (curve E)

The relationship between the half width of the PHB holes and the sample temperature is shown in FIG. 13. The results obtained in Example 5 are indicated by the line D in FIG. 13. It was confirmed that holes could be formed even at 80K.

EXAMPLE 6

The same sample as obtained in Example 4 was irradiated with a laser beam at various temperatures to form PHB holes, and the half width was measured.

The results are indicated by the line E in FIG. 13. It was confirmed that, in the sample of Example 6, holes could be formed even at 105K.

EXAMPLE 7

In refluxed propionic acid, 30 g of 4-carboxybenzaldehyde was reacted with 13.4 g of pyrrole to obtain 6.9 g of 5,10,15,20-tetra(4-carboxyphenyl)porphine. In a mixed solvent of 200 ml of distilled water and 300 ml of methanol was dissolved 10 g of polyvinyl alcohol having a polymerization degree of 2,000 and a saponification degree of 100%, and 0.066 g of the so-synthesized 5,10,15,20-tetra(4-carboxyphenyl)porphine was added to the solution. The solution was dried in a Petri dish to obtain a film having a guest concentration of $10^{-2}$M and a thickness of 0.5 mm. The sample was cooled to the liquid helium temperature and irradiated with a laser beam having a wavelength of 645 nm and an intensity of 1 mW/cm$^2$ for 30 seconds to form a PHB hole. Then, the temperature of the film was elevated to a predetermined level, the film was again cooled to the liquid helium temperature, and the half width of the PHB hole was measured.

Figure 14:
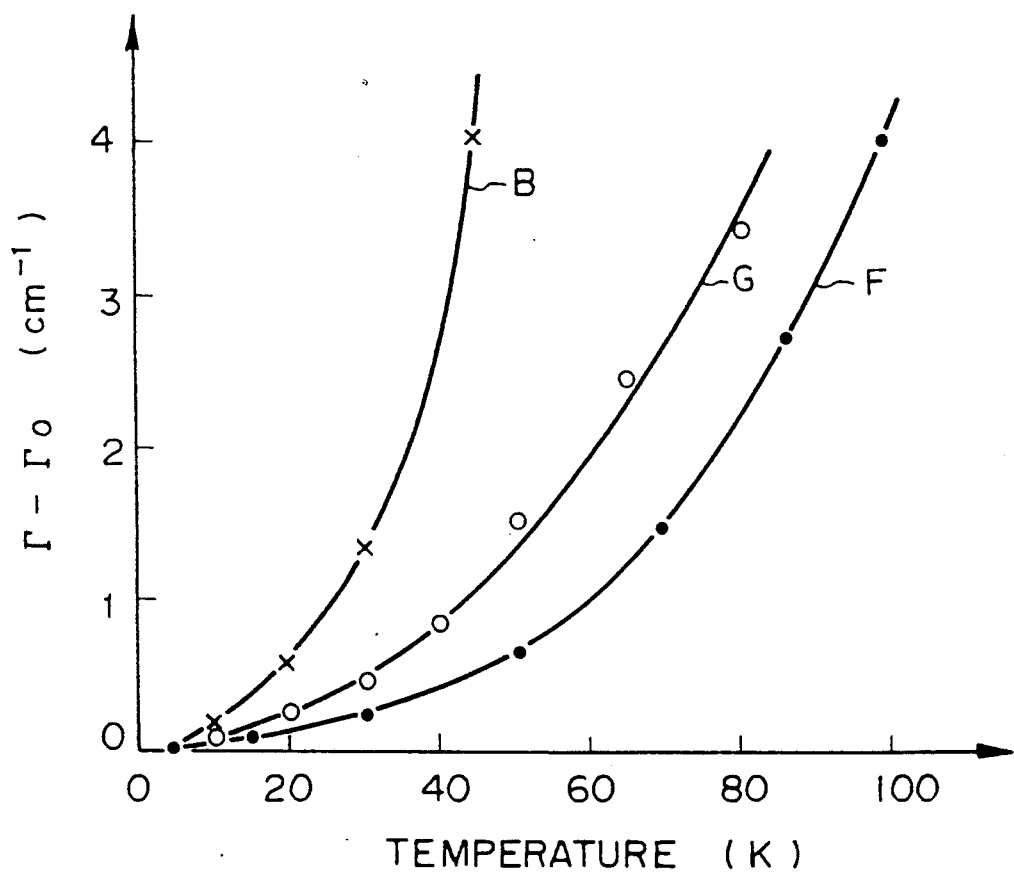
FIG. 14 is a diagram comparing performance of PHB holes formed in Examples 7 (curve F) and 8 (curve G) with PHB holes formed in Comparative Example 1 (curve B) with respect to the increase of the half width after elevation of the temperature and re-cooling; and, FIG. 15 is a diagram comparing performance of PHB holes formed in Example 9 (curve H) with PHB holes formed in Comparative Example 1 (curve B) with respect to the increase of the half width after elevation of the temperature and re-cooling.

FIG. 14 illustrates the increase of the half width after elevation of the temperature and re-cooling in comparison with the results obtained in Comparative Example 1 (curve B). In FIG. 14, the results obtained with respect to the sample of Example 7 are indicated by the curve F.

EXAMPLE 8

In 100 ml of distilled water was dissolved 10 g of sodium polystyrene sulfonate, and 0.1 g of tetrasodium 5,10,15,20-tetra(4-sulfonatophenyl)porphine dodecahydrate (supplied by Wako Pure Chemical Industries) was added to the solution. The solution was dried in a Petri dish to obtain a film having a guest concentration of $10^{-2}$M and a thickness of 0.5 mm. A PHB hole was formed in the same manner as described in Example 7. Then, the temperature of the film was elevated to a predetermined level, the film was again cooled to the liquid helium temperature, and the half width of the PHB hole was measured.

The obtained results are indicated by the curve G in FIG. 14. It is seen that the samples of Examples 7 and 8 have a smaller increase of the half width after elevation of the temperature and re-cooling and have an excellent heat stability.

EXAMPLE 9

In a mixed solution of 10 ml of tetramethoxysilane (supplied by Shin-Etsu Chemical Co.), 20 ml of methanol and 20 ml of water was dissolved 40 mg of tetrasodium 5,10,15,20-tetra(4-sulfonatophenyl)porphine dodecahydrate (supplied by Wako Pure Chemical Industries), and 0.5 ml of 0.1N aqueous ammonia was added as the catalyst to effect gelation. The gelled solution was dried in a Petri dish to obtain a film having a thickness of 0.5 mm.

The sample was cooled to the liquid helium temperature and irradiated with a laser beam having a wavelength of 645 nm and an intensity of 1 mW/cm$^2$ for 1 minute to form a PHB hole. Then, the temperature of the film was elevated to a predetermined level, the film was again cooled to the liquid helium temperature, and the half width of the PHB hole was measured.

Figure 15:
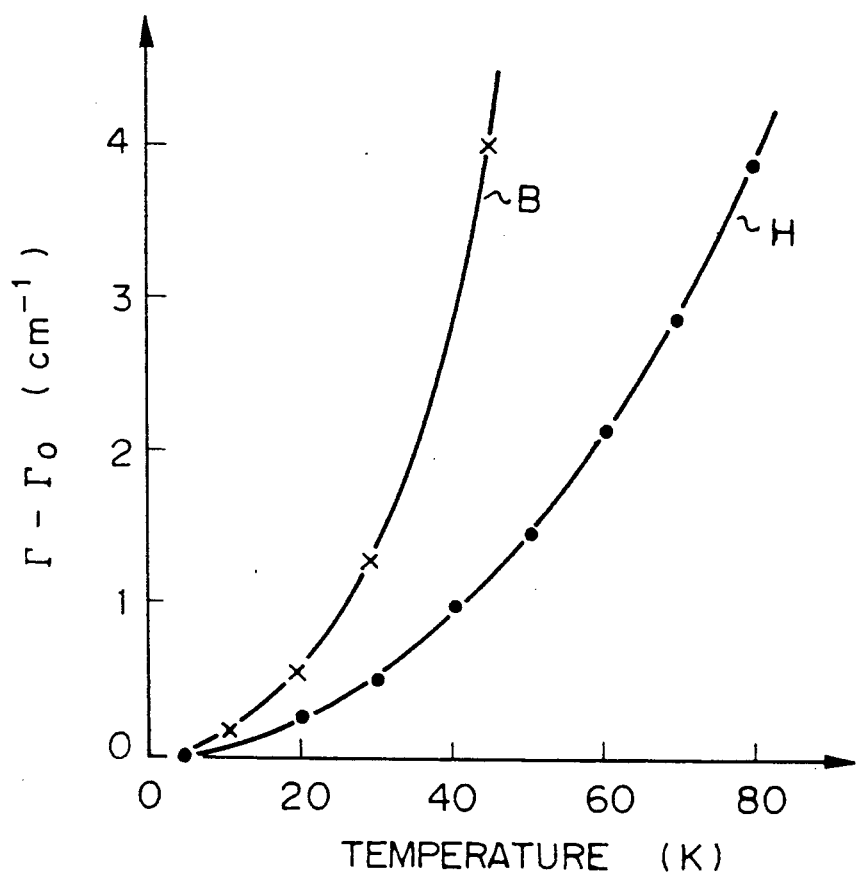

FIG. 15 illustrates the difference between ($\Gamma_0$) and ($\Gamma$) relative to the elevated temperature. The results obtained with respect to the sample of Example 9 and the results obtained with respect to the sample of Comparative Example 1 are indicated by the curves H and B, respectively. It is seen that the sample of Example 9 has a smaller increase of the half width of the PHB hole after elevation of the temperature and re-cooling and has an excellent heat stability.

EXAMPLE 10

In a mixed solution of 10 ml of tetramethoxysilane (supplied by Shin-Etsu Chemical Co.), 20 ml of methanol and 20 ml of water was dissolved 40 mg of 5,10,15,20-tetra(4-N-methylpyridinium)porphine tetraiodide (supplied by Wako Pure Chemical Industries), and 0.5 ml of 0.1N aqueous ammonia was added to the solution as the catalyst to effect gelation. The gelled solution was dried in a Petri dish to obtain a film having a thickness of 0.5 mm.

PHB holes could be formed in this film in the same manner as described in Example 9.

EXAMPLE 11

In a mixed solution of 10 ml of tetraethoxysilane (supplied by Shin-Etsu Chemical Co.), 20 ml of methanol and 20 ml of water was dissolved 40 mg of tetrasodium 5,10,15,20-tetra(4-sulfonatophenyl)porphine dodecahydrate (supplied by Wako Pure Chemical Industries), and 0.5 ml of 0.1N aqueous ammonia was added to the solution as the catalyst to effect gelation. The gelled solution was dried in a Petri dish to obtain a film having a thickness of 0.5 mm.

A PHB hole could be formed in this film in the same manner as described in Example 9.

It will be apparent that, in accordance with this invention, the guest component need not be an individual porphine derivative but may comprise a mixture comprising at least two porphine derivatives represented by the formula (I) previously set forth in this specification.

We claim:

1. An optical data recording material capable of having an optical memory created by photochemical hole burning, said material being comprised of a composition comprising a guest component dispersed in a host component as main components, wherein the guest component is a porphine derivative having at least one ionic group, represented by the following general formula (I):

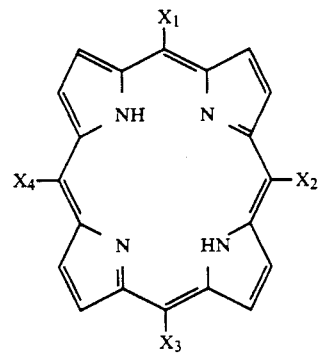

wherein at least one of $X_1$, $X_2$, $X_3$ and $X_4$ is an aryl group having an ionic group or an ionic heterocyclic group having an alkyl group of 1 to 6 carbon atoms, and the other thereof is a hydrogen atom or a non-ionic organic group, and the host component is a polymer selected from the group consisting of water-soluble organic polymers and silica glass.

2. An optical recording material as set forth in claim 1, wherein the ionic group is a cationic group.

3. An optical recording material as set forth in claim 2, wherein the cationic group is a quaternary ammonium group.

4. An optical recording material as set forth in claim 3, wherein the guest component is a 5,10,15,20-tetra(4-N,N,N-trialkylaminophenyl)porphine having 1 to 6 carbon atoms in each of the alkyl groups.

5. An optical recording material as set forth in claim 4, wherein the guest component is 5,10,15,20-tetra(4-N,N,N-trimethylaminophenyl)porphine.

6. An optical recording material as set forth in claim 1, wherein the ionic group is an anionic group.

7. An optical recording material as set forth in claim 6, wherein the anionic group is an $SO_3^-$ group.

8. An optical recording material as set forth in claim 7, wherein the guest component is 5,10,15,20-tetra(4-sulfonatophenyl)porphine.

9. An optical recording material as set forth in claim 6, wherein the anionic group is a $CO_2^-$ group.

10. An optical recording material as set forth in claim 9, wherein the guest component is 5,10,15,20-tetra(4-carbonatophenyl)porphine.

11. An optical recording material as set forth in claim 9, wherein the anionic group is a $O^-$ group.

12. An optical recording material as set forth in claim 11, wherein the guest component is 5,10,15,20-tetra(4-phenoxido)porphine.

13. An optical recording material as set forth in claim 1, wherein the ionic group is an amphoteric group.

14. An optical recording material as set forth in claim 1, wherein the heterocyclic group having an alkyl group of 1 to 6 carbon atoms is an N-alkylpyridinium group.

15. An optical recording material as set forth in claim 14, wherein the guest component is a 5,10,15,20-tetra(4-N-alkylpyridinium)porphine having 1 to 6 carbon atoms in each of the alkyl groups.

16. An optical recording material as set forth in claim 15, wherein the guest component is 5,10,15,20-tetra(4-N-methylpyridinium)porphine.

17. An optical recording material as set forth in claim 1, wherein the water-soluble polymer is polyvinyl alcohol or sodium polystyrene sulfonate.

18. An optical recording material as set forth in claim 1, wherein the silica glass is synthesized from tetramethoxysilane or tetraethoxysilane as the starting monomer.

19. An optical recording material as set forth in claim 1, wherein the concentration of the guest component is $10^{-1}$ to $10^{-5}$M as the molar concentration based on the volume of the host component.

20. An optical recording material as set forth in claim 1, wherein the guest component is a mixture comprising at least two porphine derivatives represented by the formula (I).

* * * * *